* * *

United States Patent
Fischer

(10) Patent No.: US 8,574,186 B2
(45) Date of Patent: Nov. 5, 2013

(54) DEVICE FOR MUCOSA RESECTION

(75) Inventor: Klaus Fischer, Nagold (DE)

(73) Assignee: Erbe Elektromedizin GmbH, Tübingen (DE)

( * ) Notice: Subject to any disclaimer, the term of this patent is extended or adjusted under 35 U.S.C. 154(b) by 1670 days.

(21) Appl. No.: 11/719,567

(22) PCT Filed: Nov. 18, 2005

(86) PCT No.: PCT/EP2005/012391
§ 371 (c)(1),
(2), (4) Date: May 17, 2007

(87) PCT Pub. No.: WO2006/056371
PCT Pub. Date: Jun. 1, 2006

(65) Prior Publication Data
US 2009/0149712 A1      Jun. 11, 2009

(30) Foreign Application Priority Data
Nov. 27, 2004   (DE) .......................... 10 2004 057 366

(51) Int. Cl.
*A61B 17/20* (2006.01)
*A61M 1/00* (2006.01)
(52) U.S. Cl.
USPC ........................................... 604/22; 604/118
(58) Field of Classification Search
USPC ............ 604/22, 27, 521, 118, 131, 151, 246; 606/167; 600/104
See application file for complete search history.

(56) References Cited

U.S. PATENT DOCUMENTS

| 4,097,219 | A | * | 6/1978 | Prowald ........................... 431/90 |
| 5,505,729 | A | | 4/1996 | Rau |
| 5,591,184 | A | * | 1/1997 | McDonnell et al. .......... 606/167 |
| 5,871,462 | A | * | 2/1999 | Yoder et al. ...................... 604/22 |
| 6,322,533 | B1 | | 11/2001 | Gonon |
| 6,423,027 | B1 | | 7/2002 | Gonon |
| 2001/0008961 | A1 | * | 7/2001 | Hecker et al. .................. 604/117 |
| 2002/0177802 | A1 | | 11/2002 | Moutafis et al. |
| 2004/0049207 | A1 | | 3/2004 | Goldfarb et al. |
| 2004/0087936 | A1 | | 5/2004 | Stern et al. |

FOREIGN PATENT DOCUMENTS

| DE | 225 618 | A1 | 8/1985 |
| EP | 0 258 901 | A2 | 3/1988 |
| EP | 0 551 920 | A1 | 7/1993 |
| WO | 96/24299 | A1 | 8/1996 |

* cited by examiner

*Primary Examiner* — Kevin C Sirmons
*Assistant Examiner* — Shefali Patel
(74) *Attorney, Agent, or Firm* — Dickstein Shapiro LLP

(57) ABSTRACT

To carry out a mucosa resection, a liquid is injected beneath a tissue which is then separated by means of mechanical or electrosurgical equipment. A device is provided that includes a facility for endoscopic water-jet surgery with a control device for regulating a pressure at which a water jet is discharged from a nozzle of the facility to obtain a predetermined amount of energy. An adjusting assembly is provided for setting the pressure to a first value and to a second value. The first value is so chosen that the water jet penetrates a mucosa in such a way that the mucosa is lifted from an underlying muscularis through formation of a fluid deposit. The second value is adjusted and different from the first value in such a way that the mucosa is sectionally cut through by the water jet.

11 Claims, 1 Drawing Sheet

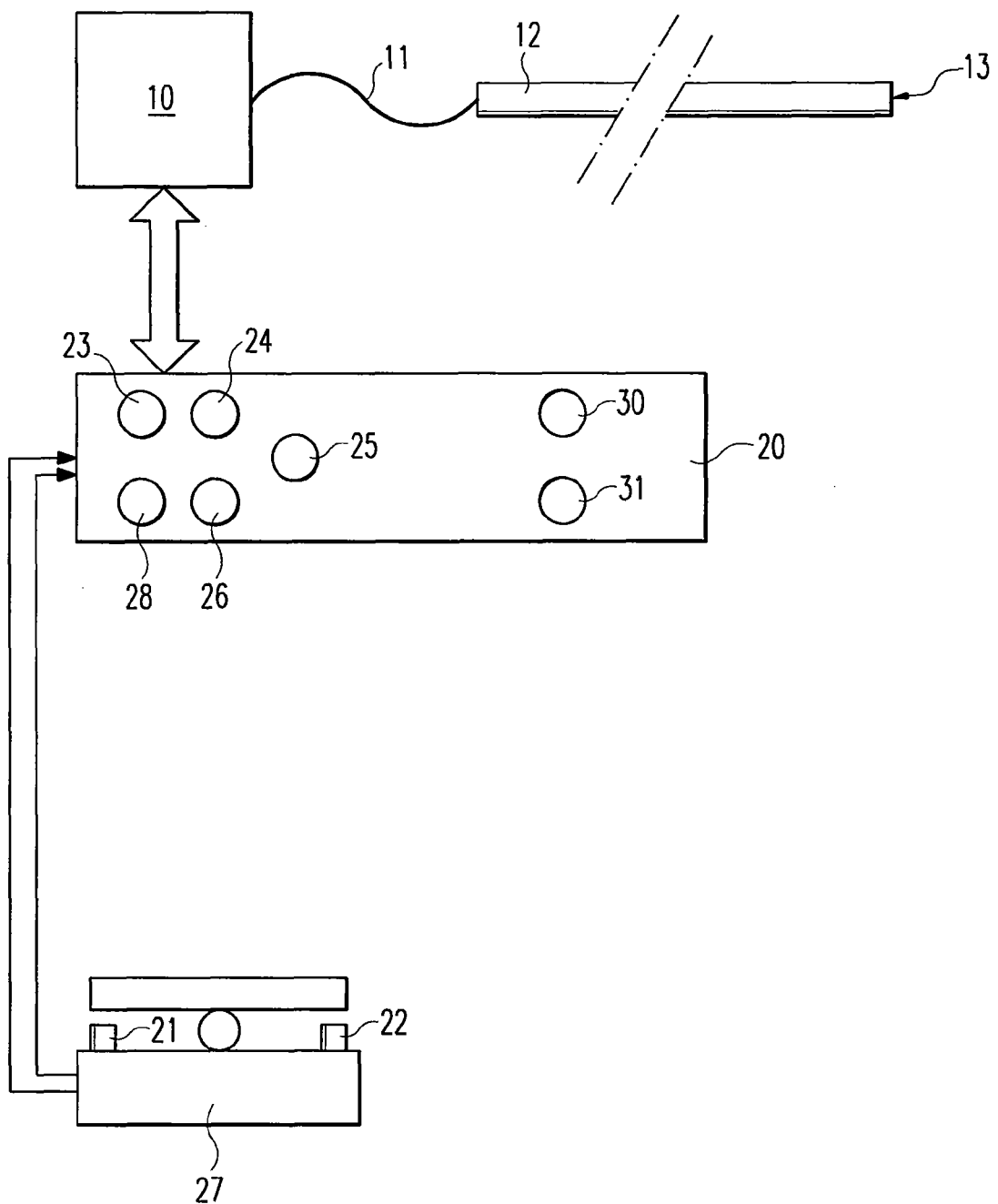

DEVICE FOR MUCOSA RESECTION

CROSS-REFERENCE TO RELATED APPLICATIONS

This application is a Section 371 of International Application No. PCT/EP2005/012391,filed Nov. 18, 2005, which was published in the German language on Jun. 1, 2006, under International Publication No. WO 2006/056371 A1 and the disclosure of which is incorporated herein by reference and which claims priority to German application No. 102004057366.2, filed Nov. 27,2004.

BACKGROUND OF THE INVENTION

The invention relates to a device for mucosa resection, in particular by means of endoscopic methods.

To treat gastrointestinal carcinomas, mucosa resections must be carried out that are usually conducted by means of endoscopic methods. Changes to the tissue are marked (dyed) upon recognition and then injected underneath with a physiological saline solution. This lifts the mucosa from the underlying layer, the muscularis. As a result, a sufficiently safe distance from the muscularis can be achieved and thus possible perforation can be avoided. The removal of the damaged mucosa can occur by means of various techniques, e.g. by snares or by IT knife. In all cases, however, it is extremely desirable to guarantee a specific, spatially restricted lifting of the mucosa and a correspondingly specific and spatially restricted separation, which is usually associated with considerable surgical effort, requiring great skill and experience on the part of the surgeon.

In particular it causes considerable problems to puncture the submucosa initially with a (flexible) needle and inject a desired (small) amount of fluid to lift the mucosa. The puncture depth, the dosage and thus the form of lifting are dependent on the operating personnel. Once the mucosa has been lifted, its separation must occur, wherein the time following the injection and the lifting of the mucosa play an essential part, since the injected fluid escapes from the submucosa and the lifting achieved consequently recede until no further separation of the damaged tissue is possible. In such cases, a new injection must be given and the attempt made again to carry out the desired separation. Particularly when a tumour lies behind a fold, a snare cannot be placed or fixed quickly enough around the lesion.

BRIEF SUMMARY OF THE INVENTION

The object of the invention is to provide a device for mucosa resection, by means of which mucosal tissue can be safely removed in a simple manner.

According to the present invention there is provided a device for endoscopic mucosa-resection, comprising a facility for endoscopic water-jet surgery with a control device for regulating the pressure at which a water jet is discharged from a nozzle to obtain a predetermined amount of energy, and with an adjusting means for setting the pressure to a first value, at which the water jet penetrates the mucosa in such a way that it is lifted from the underlying muscularis through the formation of a fluid deposit, and to a second value, different from the first value, at which the mucosa is sectionally cut through by the water jet.

Thus, both the injection to lift the mucosa and the severing of the tissue are effected by means of a single instrument and, indeed, merely by a suitable adjustment of the pressure.

A further advantage of the device according to the invention is that, as a result of the severing, at least part of the fluid effecting the separation replaces fluid escaping from the deposit and thus achieves the lifting.

Preferably, the adjusting means is configured in such a way that a predetermined amount of fluid is discharged upon setting the pressure to the first value and actuating a first starting switch. This enables a very simple and precise dosage of the amount of fluid to occur, which lifts the mucosa.

The adjusting means is further preferably configured in such a way that, upon setting the pressure to a second value and actuating a second starting switch, the fluid is discharged in an essentially continuous manner while the second starting switch is operated. This hands the cutting of the tissue completely over to the surgeon.

The adjusting means is further preferably configured in such a way that the first pressure can be adjusted independently of the second pressure. As a result, the pressure required to lift the mucosa and the pressure required to cut it can be adapted in each case to the physiological circumstances.

It is also possible to equip the adjusting means with a ratio setting mechanism, which permits a predetermined ratio of the first pressure to be set in relation to the second. In particular, when a peak pressure setting mechanism is provided, a quick adjustment to changing tissue conditions can be made.

The second pressure can preferably be adjusted in several stages to adapt to different tissue types, guaranteeing easy operability through the choice of few values. The pressures in the different stages can preferably be adjusted independently of each other, which in turn facilitates the handling during an operation.

Preferably a display mechanism is provided to indicate different operating modes, in particular in relation to a currently set pressure value or also a previously set pressure value for lifting or cutting through the mucosa, so that the surgeon can easily see the values he has so far been operating with or the values that are currently set.

To operate the device, a foot switch is preferably provided for optional setting of the first or second pressure, that is, for switching between injecting and cutting. In this case, it is also possible to work with a single starting switch that will trigger the particular operation (injection/separation).

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 is a schematic representation of an embodiment of a device according to the present invention.

DETAILED DESCRIPTION OF THE INVENTION

As shown in the drawing, in a device according to the invention a water-jet facility 10 is provided that may be of a conventional type. Water, which in practice comprises a physiological saline solution, is supplied to a probe 12, which can be introduced into the working channel of an endoscope, via a supply line 11. The water jet issues from a nozzle 13 at the distal end of the probe 12.

To control the water-jet facility 10 an adjusting means 20 is provided which is equipped with various setting mechanisms. In particular, a first pressure setting mechanism 23 and a second pressure setting mechanism 24 are provided here for pre-selecting the first or second pressure. The ratio of the first to the second pressure can be set by means of a setting mechanism 25 and the peak pressure can be set by means of a mechanism 26. These pressure settings are not all independent of each other, the result being that setting occurs either by the setting mechanisms 23 and 24 or by setting of the mechanisms 25, 26.

In both cases, the injection duration upon application of the first pressure is set by means of a setting mechanism 28.

A foot switch 27 is provided for actuation, which has a first starting switch 21 and a second starting switch 22. Depending on which of the two starting switches 21 or 22 is actuated, the device operates using the first or second pressure. It is also possible, of course, to configure the foot switch 27 in such a way that it only selects the pressure, while the starting signal is given by another switch, e.g. a hand-operated switch. It is likewise possible to provide appropriate hand switches instead of a foot switch.

Finally, the adjusting means 20 has further display mechanisms 30 and 31 for indicating the first or second pressure, wherein these display mechanisms are configured in such a way that rapid monitoring to determine which of the two pressures is set is as much facilitated as exact monitoring of the set pressure (as the measured value).

In one alternative embodiment of the invention not depicted in the FIGURE, a means is provided for allowing the water jet with the first pressure to issue from a different nozzle 13 to the water jet with the second pressure. As a result it is possible to select variably not only the jet diameter but also the jet direction, depending on whether tissue is to be injected or separated.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A device for endoscopic mucosa resection, comprising:
   a facility for endoscopic water-jet surgery comprising a nozzle for discharge of a fluid jet;
   a control device for regulating a pressure with which the fluid jet discharged from the nozzle to obtain a predetermined amount of energy;
   an adjusting means for setting the pressure of the fluid jet to a first pressure value, at which the fluid jet penetrates a mucosa to lift the mucosa from an underlying muscularis by formation of a fluid deposit, and to a second pressure value, different from the first pressure value, at which the fluid jet sectionally cuts through the mucosa; and
   a first starting switch, wherein the adjusting means is configured to discharge a predetermined amount of the fluid from the nozzle when the pressure is set to the first pressure value and the first starting switch is actuated.

2. The device according to claim 1, further comprising a second starting switch, wherein the adjusting means is configured to discharge the fluid from the nozzle in a substantially continuous manner when the pressure is set to the second pressure value and while the second starting switch is actuated.

3. The device according to claim 1, wherein the adjusting means allows the first pressure value to be adjusted independently of the second pressure value.

4. The device according to claims claim 1, wherein the adjusting means has a ratio setting mechanism adapted to set a predetermined ratio of the first pressure value relative to the second pressure value.

5. The device according to claim 4, further comprising a peak pressure setting mechanism that sets a maximum pressure with which the fluid jet is discharged from the nozzle.

6. The device according to claim 1, wherein the second pressure value is adjustable in several stages to adapt the device for use with different tissue types.

7. The device according to claim 6, wherein the pressure in each stage of the several stages is adjustable independently of the pressure in each other stage of the several stages.

8. The device according to claim 1, further comprising a display mechanism adapted to indicate whether the device is operating at the first pressure value or the second pressure value.

9. The device according to claim 1, wherein the adjusting means comprises a foot switch adapted for optional selection of the first or second pressure values.

10. A device for endoscopic mucosa resection, comprising:
    a facility for endoscopic water-jet surgery comprising a nozzle for discharge of a fluid jet;
    a control device for regulating a pressure with which the fluid jet is discharged from the nozzle to obtain a predetermined amount of energy; and
    an adjusting means for setting the pressure of the fluid jet to a first pressure value, at which the fluid jet penetrates a mucosa to lift the mucosa from an underlying muscularis by formation of a fluid deposit, and to a second pressure value, different from the first pressure value, at which the fluid jet sectionally cuts through the mucosa, wherein the adjusting means has a ratio setting mechanism adapted to set a predetermined ratio of the first pressure value relative to the second pressure value.

11. The device according to claim 10, further comprising a peak pressure setting mechanism that sets a maximum pressure with which the fluid jet is discharged from the nozzle.

* * * * *

UNITED STATES PATENT AND TRADEMARK OFFICE
CERTIFICATE OF CORRECTION

PATENT NO.         : 8,574,186 B2
APPLICATION NO. : 11/719567
DATED              : November 5, 2013
INVENTOR(S)        : Klaus Fischer Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1668 days.

Signed and Sealed this

Twenty-second Day of September, 2015

Michelle K. Lee
*Director of the United States Patent and Trademark Office*